United States Patent [19]

Asakawa et al.

[11] 4,305,842

[45] Dec. 15, 1981

[54] PREPARATION OF IMPROVED CATALYST COMPOSITION

[75] Inventors: Kazuo Asakawa; Yasuo Yamamoto; Shuji Ebata; Tadasi Nakamura, all of Niigata, Japan

[73] Assignee: Mitsubishi Gas Chemical Company, Inc., Tokyo, Japan

[21] Appl. No.: 119,778

[22] Filed: Feb. 8, 1980

[30] Foreign Application Priority Data

Feb. 10, 1979 [JP] Japan .................................. 54/13846

[51] Int. Cl.$^3$ .......................... B01J 21/02; B01J 27/24
[52] U.S. Cl. .................................. 252/432; 252/438
[58] Field of Search ................................ 252/432, 438

[56] References Cited

U.S. PATENT DOCUMENTS

| | | | |
|---|---|---|---|
| 3,853,922 | 12/1974 | Yamaguchi et al. | 252/432 X |
| 3,939,191 | 2/1976 | Asano et al. | 252/432 X |
| 3,971,735 | 7/1976 | Asano et al. | 252/432 X |

FOREIGN PATENT DOCUMENTS

| | | | |
|---|---|---|---|
| 988072 | 4/1976 | Canada | 252/438 |
| 1145142 | 3/1963 | Fed. Rep. of Germany | 252/438 |
| 1159035 | 7/1969 | United Kingdom . | |
| 1286970 | 8/1972 | United Kingdom . | |

*Primary Examiner*—Delbert E. Gantz
*Assistant Examiner*—William G. Wright
*Attorney, Agent, or Firm*—Wenderoth, Lind & Ponack

[57] ABSTRACT

A process for preparing a catalyst composition containing a copper oxide, a zinc oxide and an aluminum oxide as essential components and, if desired, containing a boron oxide, which comprises the following steps:

(a) a step of precipitating from an aqueous solution of a water-soluble copper salt, which solution, if desired, may contain a water-soluble boron compound, a copper component, together with a boron component if the boron compound is present, with the use of ammonium carbonate or ammonium bicarbonate as a precipitant;

(b) a step of precipitating from an aqueous solution of a water-soluble zinc salt, which solution, if desired, may contain a water-soluble boron compound, a copper component, together with a boron component if the boron compound is present, with the use of an alkali hydroxide as a precipitant; and (c) a step of calcing a mixture of the precipitates obtained in the steps (a) and (b) in the presence of an alumina precursor compound.

The catalyst thus obtained is useful in synthesizing methanol from a mixed gas comprising carbon monoxide and/or carbon dioxide and hydrogen.

21 Claims, No Drawings

PREPARATION OF IMPROVED CATALYST COMPOSITION

This invention relates to a catalyst composition having improved properties. More specifically, the invention relates to a process for preparing a catalyst composition stably with good reproducibility, said catalyst showing superior activity at relatively low temperatures and low pressures and having high mechanical strengths such as resistance to abrasion and resistance to compression and being suitable especially for use in synthesizing methanol from a mixed gas comprising carbon monoxide and/or carbon dioxide and hydrogen; a catalyst composition prepared by said process; and the use of said catalyst composition.

Generally, copper-zinc type or copper-zinc-chromium type catalysts have hitherto been used as catalysts for synthesizing methanol by a vapor-phase method from carbon monoxide and/or carbon dioxide and hydrogen. Synthesis of methanol by use of these catalysts, however, generally needs high temperatures of above 280° C. and high pressures higher than 150 atmospheres and gives low conversions to methanol. Said catalysts, moreover, have defects such that they are poor in heat resistance and durability and cannot withstand long-term use.

In recent years, to save energy such as for pressurization, the demand has increased for the development of techniques for synthesizing methanol under relatively low pressures of from 50 to 150 atmospheres, and catalysts with better activities have become necessary. To satisfy said demand, there have been proposed methanol-synthesizing catalysts comprising oxides of copper, zinc and aluminum (see British Pat. No. 1,159,035 and British Pat. No. 1,286,970; these catalysts are called hereinafter "Cu-Zn-Al three-component catalysts") and methanol-synthesizing catalysts comprising oxides of copper, zinc, aluminum and boron (see U.S. Pat. No. 3,971,735; the catalysts are referred to hereinafter as "Cu-Zn-Al-B four-component catalysts"). These proposed catalysts, however, have all been produced by a co-precipitation method and are commercially not fully satisfactory in properties such as catalytic activity and mechanical strengths, thus still leaving room for improvement.

Therefore, the main object of the present invention is to provide a catalyst composition having a markedly improved catalytic activity and superior mechanical strengths and suitable especially as a catalyst for synthesis of methanol.

Another object of the present invention is to provide a novel process for preparing with good reproducibility a Cu-Zn-Al three-component or Cu-Zn-Al-B four-component catalyst composition which shows excellent catalytic activity at relatively low temperatures and low pressures, which is low in abrasion rate and high in resistance to compression, and which has excellent moldability.

A further object of the present invention is to provide a catalyst composition produced by said novel process.

A still further object of the present invention is to provide a process for synthesizing methanol with the use of a catalyst composition prepared by the above-described novel process.

Other objects and advantages of the present invention will become apparent from the following description.

According to the present invention, it has been found that the above-described objects of the present invention can be attained not by co-precipitating copper and zinc components in the preparation of said Cu-Zn-Al three-component or Cu-Zn-Al-B four-component catalyst, but by separately precipitating copper and zinc components in said preparation with the use of specific substances as precipitants for the copper and zinc components, respectively, in precipitating these components from their soluble salts. This finding has led the present inventors to complete the present invention.

The present invention in a major aspect provides a process for preparing a catalyst composition consisting essentially of copper, zinc and aluminum oxides and if desired, containing a boron oxide, which comprises the following steps:

(a) a step of precipitating from an aqueous solution of a water-soluble copper salt which, if desired, may contain a water-soluble boron compound, a copper component, together with a boron component if said boron compound is present, with the use of ammonium carbonate or ammonium bicarbonate as a precipitant;

(b) a step of precipitating from an aqueous solution of a water-soluble zinc salt which, if desired, may contain a water-soluble boron compound, a zinc component, together with a boron component if said boron compound is present, with the use of an alkali hydroxide as a precipitant; and (c) a step of calcining in the presence of an alumina precursor compound a mixture of the precipitates obtained in the steps (a) and (b).

The above process of the present invention is characterized in that the copper and zinc components are not co-precipitated from their soluble salts, but are precipitated separately from their soluble salts with the use of precipitants peculiar thereto.

Examples of the water-soluble copper salt used in the step (a) include any water-soluble salts of copper that have been hitherto used in the production of Cu-Zn-Al three-component and Cu-An-Al-B four-component catalysts. For example, there are listed cupric nitrate and cupric acetate. Of these salts, the salts that do not contain elements such as halogen or sulfur capable of becoming catalyst poisons are preferred, and cupric nitrate is particularly suitable.

Said water-soluble copper salt is subjected to precipitation with an alkaline precipitant from a solution in an aqueous medium such as water (deionized water). The concentration of the water-soluble copper salt in the aqueous solution is not critical and can be varied widely according to the type of the copper salt used, and so forth. Generally, it is advantageous that the concentration be 0.1 to 2.0 mol/l (much lower than the solubility), more preferably, 0.25 to 1.0 mol/l.

The alkaline precipitant for precipitating the copper component as an insoluble solid from the aqueous solution of the water-soluble copper salt is, in the present invention, ammonium carbonate or ammonium bicarbonate. If the precipitate-forming reaction in the step (a) of the present invention is illustrated with cupric nitrate and ammonium bicarbonate taken as examples, the reaction can proceed in accordance with the following reaction formula

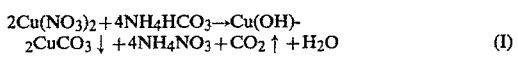

$$2Cu(NO_3)_2 + 4NH_4HCO_3 \rightarrow Cu(OH)_2 \cdot CuCO_3 \downarrow + 4NH_4NO_3 + CO_2 \uparrow + H_2O \qquad (I)$$

thereby precipitating the basic copper carbonate [Cu(OH)$_2$CuCO$_3$] as a water-insoluble solid. Ammonium carbonate or ammonium bicarbonate used in the precipitate-forming reaction may be used as such or as an aqueous solution. In either case, it is generally advantageous to use ammonium carbonate or ammonium bicarbonate in an amount of at least 0.8 equivalent, preferably 1.0 to 2.0 equivalents, more preferably 1.0 to 1.3 equivalents, per equivalent of the copper salt to be precipitated.

The temperature of the precipitate-forming reaction is not critical and can be varied over a wide range. Generally, the precipitate-forming reaction can be performed at ambient temperature or may be carried out, if desired, with heating at a temperature of up to about 60° C., preferably up to about 50° C. Under these conditions, the precipitate-forming reaction proceeds very smoothly, and can be completed virtually quantitatively normally in about 15 minutes. The resulting slurry containing an insoluble copper component dispersed therein can be subjected as such to the treatment of the subsequent step, but usually, it is advantageous that prior to treatment in the subsequent step, the slurry be aged at a temperature preferably of about 60° to about 100° C., particularly of about 70° to about 90° C., for at least 5 minutes, usually 10 to 60 minutes.

In the aforementioned step (b), the zinc component is precipitated from its water-soluble salt. As the water-soluble zinc salt there can be used any water-soluble zinc salts which have usually been used in the preparation of Cu-Zn-Al three-component or Cu-Zn-Al-B four-component catalysts. Examples include water-soluble zinc salts such as zinc nitrate and zinc acetate. Of these salts, preferred are those not containing elements that become catalyst poisons, such as halogen or sulfur. Particularly preferred is zinc nitrate.

The water-soluble zinc salt is subjected to precipitation with an alkaline precipitant from a solution in an aqueous medium such as water (deionized water). The concentration of the water-soluble zinc salt in the aqueous solution is not critical and can be varied widely according to the type of the zinc salt used, and so forth. Generally, the advantageous concentration is 0.1 to 2.0 mol/l (much lower than the solubility), preferably 0.2 to 1.0 mol/l.

The alkaline precipitant used in the present invention for precipitating the zinc component as an insoluble solid from the aqueous solution of the water-soluble zinc salt is an alkali hydroxide, namely, an alkali metal hydroxide such as potassium hydroxide, sodium hydroxide, or lithium hydroxide. If the precipitate-forming reaction in the step (b) of the present invention is described with zinc nitrate and sodium hydroxide taken as typical examples, the reaction proceeds in accordance with the following reaction formula

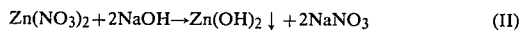

$$Zn(NO_3)_2 + 2NaOH \rightarrow Zn(OH)_2 \downarrow + 2NaNO_3 \qquad (II)$$

whereby the zinc hydroxide [Zn(OH)$_2$] can be precipitated as a water-soluble solid. The alkali hydroxide used in the precipitate-forming reaction can be used as it is or as an aqueous solution. In either case, it is generally advantageous to use the alkali hydroxide in an amount of at least 0.8 equivalent, preferably 0.9 to 1.5 equivalents, more preferably 0.9 to 1.2 equivalents, per equivalent of the zinc salt to be precipitated.

The temperature of the precipitate-forming reaction is not critical and can be varied widely, but generally, the reaction can be performed at ordinary temperature or may be carried out, if desired, with heating at a temperature of up to about 60° C., preferably up to about 50° C. Under these conditions, the precipitate-forming reaction proceeds very smoothly and can be completed substantially quantitatively normally in about 15 minutes. The resulting slurry can be subjected unchanged to the subsequent step, but it is advantageous that before it is treated in the subsequent step, the slurry be aged by maintaining it at a temperature preferably of about 60° to about 100° C., particularly of about 70° to about 90° C., for at least 5 minutes, normally for 10 to 60 minutes.

The slurries formed by the precipitation in the steps (a) and (b) may be aged separately from each other. Generally, it is convenient because of labor saving to mix the slurry of the step (a) and the slurry of the step (b) and then age the mixture under the above-mentioned conditions, as will be described later.

When the present invention is aimed at producing a Cn-Zn-Al-B four-component catalyst, it is possible to dissolve a water-soluble compound of boron in one of or both of the aqueous solution of the water-soluble copper salt of the step (a) and the aqueous solution of the water-soluble zinc salt of the step (b), prior to the precipitate-forming reaction of the step (a) and/or step (b). It is particularly preferable, however, to dissolve the water-soluble compound of boron in the aqueous solution of the zinc salt, because that compound has the action of preventing a precipitate of the zinc component from gelling.

As the water-soluble compound of boron can be employed any water-soluble boron compounds which have hitherto been used in the preparation of Cu-Zn-Al-B four-component catalysts. Examples thereof include boric acid, borax, ammonium borate, sodium metaborate and potassium borate. Of course, it is desirable for these water-soluble boron compounds to contain no elements, such as halogen or sulfur, which act as catalyst poisons. The particularly preferable water-soluble boron compounds are boric acid and borax.

The amount of the water-soluble boron compound dissolved can be varied depending on the content of the boron component required to be contained in said four-component catalyst. Generally, the water-soluble boron compound can be added suitably to the aqueous solution of the copper salt and/or the aqueous solution of the zinc salt so that its amount, expressed as a B/Zn atomic ratio, is 0.1–1.5, preferably 0.2–1.0, more preferably, 0.25–0.8, to the zinc salt.

The mechanism by which a precipitate of the water-soluble boron compound is formed has not been clearly known, but is supposed to utilize physical adsorption by precipitates of the copper and zinc components.

When the water-soluble boron compound is used, therefore, there is no need to change the amount of the precipitant used, and the steps (a) and (b) can be carried out under substantially the same conditions as those without the use of the water-soluble boron compound.

According to the present invention, the reactions for forming precipitates of the copper and zinc components in the steps (a) and (b) can be carried out continuously in a reaction vessel in the sequence step (a)→step (b) or step (b)→step (a) as far as the two reaction are performed separately, namely, as far as no co-precipitation reaction substantially takes place; alternatively, the two steps may be conducted as separate steps in separate reaction vessels.

When the two precipitate-forming reactions are to be performed sequentially in a single reactor, it is possible to add chemicals in the following sequence, for instance, thereby to perform the precipitate-forming reactions sequentially. In the following description, solution A means an aqueous solution of a water-soluble copper salt, if desired, containing a water-soluble boron compound; agent B refers to ammonium carbonate or ammonium bicarbonate or an aqueous solution thereof; solution C means an aqueous solution of a water-soluble zinc salt, if desired, containing a water-soluble boron compound; and agent D means an alkali hydroxide or an aqueous solution thereof.

(i)
Solution A ⟶ Agent B [step (a)] ⟶
Solution C ⟶ Agent D [step (b)]
[aging]

(ii)
Solution A ⟶ Agent B [step (a)] ⟶
Agent D ⟶ Solution C [step (b)]
[aging]

(iii)
Agent B ⟶ Solution A [step (a)] ⟶
Agent D ⟶ Solution C [step (b)]
[aging]

(iv)
Agent B ⟶ Solution A [step (a)] ⟶
Solution C ⟶ Agent D [step (b)]
[aging]

(v)
Solution C ⟶ Agent D [step (b)] ⟶
Solution A ⟶ Agent B [step (a)]
[aging]

(vi)
Solution C ⟶ Agent D [step (b)] ⟶
Agent B ⟶ Solution A [step (a)]
[aging]

(vii)
Agent D ⟶ Solution C [step (b)] ⟶
Agent B ⟶ Solution A [step (a)]
[aging]

(viii)
Agent D ⟶ Solution C [step (b)] ⟶
Solution A ⟶ Agent B [step (a)]
[aging]

In the above-mentioned procedure, solution A, agent B, solution C and agent D are not to be continuously added, and it is very desirable to initiate the addition of chemicals for the subsequent step after the precipitate-forming reaction in the preceding step has been substantially complete. In the procedure (i), for instance, solution A is charged into a reactor, and agent B is added, whereafter a precipitate-forming reaction according to step (a) is performed under the aforementioned conditions; when the precipitate-forming reaction is complete, solution C and then agent D are added to the resulting slurry, whereafter a precipitate-forming reaction in accordance with step (b) is performed. The same is true of the other procedures (ii) to (viii).

The completion of the precipitate-forming reaction can be confirmed, for instance, by the fact that a precipitate is no more formed even when the precipitant is further added.

In said procedure, aging may be carried out during the period between the preceding step and the succeeding step, but it is preferred to perform aging after completion of the precipitate-forming reaction of the succeeding step.

When aging is to be carried out, it has been found preferable in physical properties of the final catalyst to perform the precipitate-forming reaction at a relatively low temperature of from ambient temperature to 60° C., preferably at ambient temperature, and then perform aging by maintaining a relatively high temperature in the range of from about 60° to about 100° C., preferably from about 70° to about 90° C.

As an alternative method, the step (a) and step (b) of the present invention can be effected in separate reaction vessels. In this case, no particular restrictions are imposed on the sequence of charging of solution A and agent B into the reactor in the step (a) or on the sequence of charging of solution C and agent D into the reactor in the step (b), and the charging may be performed in any sequence. In this case, it is possible to perform aging under the aforementioned conditions after completion of the precipitate-forming reaction in each of the steps, but it is advantageous to mix slurries formed by the respective steps when the precipitate-forming reaction in each step has been complete, and then to age the mixture if desired.

In the process of the present invention, the product of the precipitate-forming reaction of the step (a) and the product of the precipitate-forming reaction of the step (b) are mixed with stirring, preferably, in the slurried state, as described above. Desirably, the mixing with stirring is performed as intimately as possible; for instance, it is convenient to carry out the mixing in a device such as a stirrer having a baffle.

The precipitation product-containing slurry mixture is, if desired, aged as mentioned earlier, and then, the reaction solvent is separated therefrom by ordinary means such as filtration. The separated product is washed thoroughly to remove the remaining precipitant, and then calcined in the presence of an alumina precursor compound.

In the present specification, the "alumina precursor compound" refers to a compound which gives alumina upon thermal decomposition under the calcination conditions to be described later and which after decomposition does not leave a substance poisonous to the catalyst of the present invention, such as sulfur or halogen. The alumina precursor compound includes the so-called alumina sol, or aluminum hydroxide or the like which is obtained from an aqueous solution of a water-soluble aluminum compound (e.g. sodium aluminate, aluminum acetate or aluminum nitrate) by precipitation through means such as hydrolysis or treatment with a precipitant such as an alkali.

It is usually preferred to add the alumina precursor compound in the form of alumina sol to the aforesaid precipitation product mixture. If desired, however, the alumina precursor compound may be made present in the mixed precipitation products by rendering a water-soluble aluminum salt, such as sodium aluminate, aluminum acetate or aluminum nitrate, co-present in the reaction system of the precipitate-forming reaction in the step (a) and/or step (b), and causing the alumina precursor compund, which is water-insoluble, to precipitate together with the copper component and/or zinc component.

When alumina sol is to be added to the mixed precipitation products, the alumina sol may be one having an average particle diameter of 1 micron or less, preferably, 0.2 micron or less, for good dispersibility.

The amount of the alumina precursor compound to be made present in the mixed precipitation products can be varied depending on the proportion of the aluminum component required of the final catalyst, as in the aforementioned description. Generally, that amount can be a value, calculated as a metal atom ratio to the copper component in the precipitate mixture, (Cu/Al), in the range of from 3/1 to 70/1, preferably from 5/1 to 65/1, more preferably from 7/1 to 50/1.

The precipitate mixture having the alumina precursor compound thus included therein is then subjected, if desired, to treatments such as kneading and drying as usual, followed by calcination. The calcination can be performed by a method known per se. For instance, the calcination can be effected by heating at a temperature of at least 300° C., preferably at 330° to 400° C., usually for about 0.5 to 3 hours in an atmosphere such as air, $N_2$, or combustion gas in a calcination furnace such as an electric furnace or a gas calcination furnace. By this calcination, the copper component, the zinc component, the alumina precursor compound and the boron component are each converted into the oxide form.

The so obtained catalyst is molded by a method comprising pulverizing it, pre-molding the pulverized product by a molding machine, further pulverizing the pre-molded product, and then compression molding it into tablets, whereby there can be afforded a catalyst composition having a sufficient mechanical strength as an industrial catalyst.

The catalyst produced by the process of the present invention that has been described above comprises a Cu-Zn-Al three-component catalyst or a Cu-Zn-Al-B four-component catalyst. In the case of the Cu-Zn-Al three-component catalyst, the proportions of the copper, zinc and aluminum components are on a metal atom ratio basis: copper, 30–70%, preferably, 40–60%; zinc, 15–50%, preferably, 20–40%; aluminum, 1–20%, preferably, 4–16%. In the case of the Cu-Zn-Al-B four-component catalyst, the proportions of the copper, zinc, aluminum and boron components are on an element atom ratio basis: copper, 30–70%, preferably 40–60%; zinc, 15–50%, preferably 20–40%; aluminum, 1–16%, preferably 3–12%; and boron, 0.1–5.0%, preferably 0.2–3.0%.

In the catalyst composition provided by the present invention, the copper, zinc, aluminum and boron elements are each present usually in the form of oxide.

The catalyst composition of the present invention thus prepared permits small amounts of metal atoms to be incorporated in addition to the above-described components; for instance, alkali metal atoms may be incorporated in amounts of 100 to 400 ppm.

The catalyst composition prepared by the process of the present invention is, as is usually practiced, subjected to an activation treatment, for example, by reduction with hydrogen, and then, can be used as a catalyst for a reaction for synthesizing methanol from a mixed gas containing carbon monoxide and/or carbon dioxide and hydrogen, or a reaction such as a carbon monoxide conversion reaction, a hydrogenation reaction or a methanol decomposition reaction.

The activation treatment of the catalyst composition in accordance with the present invention is performed by a customary method. For example, the activation can be carried out by using a reducing atmosphere such as a starting gas for synthesis of methanol; raising a temperature slowly from about 140° C. to avoid a radical generation of heat by a reduction reaction; and finally maintaining the temperature at 240° C. for 3 hours for reduction.

The so activated catalyst composition according to the present invention is suitable particularly as a reaction catalyst for use in synthesizing methanol from a mixed gas containing carbon monoxide and/or carbon dioxide and hydrogen. The reaction for synthesis of methanol with the use of the catalyst composition in accordance with the present invention can be carried out by a method known per se, for instance, the method described in U.S. Pat. No. 3,971,735. For example, the synthesis reaction can be performed by feeding said mixed gas to the reaction system at a pressure of 20 to 300 atmospheres, preferably 30 to 150 atmospheres, at a temperature of 150° to 300° C., preferably 200° to 280° C., at a space velocity of 2,000 to 50,000 $hr^{-1}$.

The catalyst composition afforded by the process of the present invention has various excellent advantages to be described below, as compared with the conventional catalysts of the same type as the instantly claimed catalyst composition. Thus, the present catalyst composition is very suitable as a catalyst for synthesis of methanol.

(a) It shows superior activity at relatively low temperatures and relatively low pressures.

(b) It has a low abrasion rate and a superior compressive strength. Its small difference between the abrasion rate before reduction and that after reduction, in particular, is advantageous in practical use.

(c) It has excellent moldability. It gains an industrially sufficient mechanical strength merely by pre-molding it once prior to the compression molding.

The present invention will be explained in greater detail with reference to Examples, Comparative Example and Referential Examples below.

EXAMPLE 1

An aqueous solution of cupric nitrate was prepared by dissolving 130 kg of cupric nitrate (trihydrate) in 946 liters of deionized water, and the solution was maintained at a temperature of about 30° C. Also, an aqueous solution of zinc nitrate was prepared by dissolving 120 kg of zinc nitrate (hexahydrate) in 686 liters of deionized water, and the solution was maintained at a temperature of about 30° C.

Separately, a solution obtained by dissolving 93.6 kg of ammonium bicarbonate in 1089 liters of deionized water was charged into a 6000-liter reaction vessel, and the temperature of the solution was maintained at about 30° C. With this solution stirred, said aqueous solution of cupric nitrate was added thereto, and the mixture was reacted for 15 minutes at 30° C. to obtain a slurry. To the slurry was added, with stirring, an aqueous solution of sodium hydroxide held at a solution temperature of 30° C. that had been formed by dissolving 32.3 kg of sodium hydroxide in 775 liters of deionized water, and then, said aqueous solution of zinc nitrate was further added, followed by continuing stirring for 10 minutes, to perform the reaction. Then, the temperature of the solution in the reaction vessel was raised to 80° C., and stirring was continued for 30 minutes for aging, followed by allowing the mixture to cool.

The resulting slurry was filtered in accordance with a customary method, and washed with water. To the filter cake was added 40 kg of alumina sol (average particle diameter: $0.1\mu$), and the mixture was kneaded for 40 minutes by a kneader. After the kneading, the resulting mass was dried for 17 hours at 100° C., then placed in a calcination furnace, and calcined for about 2.5 hours at 370° C. After the calcination, the resultant catalyst was pulverized to a size of 14 mesh or less, and mixed with 3% of graphite. The mixture was premolded, pulverized again to 14 mesh, and then subjected to compression molding. The so obtained Cu-Zn-Al three-component catalyst (metal atom ratio Cu:Zn:Al=55:41:4) is referred to hereinafter as "catalyst A".

A Cu-Zn-Al-B four-component catalyst (metal atom ratio Cu:Zn:Al:B=55:40.5:4.2:0.3) was prepared in the same manner as described above except that 12.5 kg of boric acid was additionally dissolved in the aforementioned aqueous solution of zinc nitrate. This catalyst is referred to hereinafter as "catalyst B".

EXAMPLE 2

The procedure of Example 1 was repeated except that the chemicals were added in the sequence of solution C, agent D, solution A and agent B. A Cu-Zn-Al three-component catalyst obtained without the use of the boron component is called "catalyst C," while a Cu-Zn-Al-B four-component catalyst obtained with the addition of the boron component is called "catalyst D".

EXAMPLE 3

A solution of 93.6 kg of ammonium bicarbonate dissolved in 1089 liters of deionized water was charged into a reaction vessel, and the temperature of the solution was maintained at 30° C. Separately, a solution of 130 kg of cupric nitrate (trihydrate) in 946 liters of deionized water was formed and maintained at 30° C. This solution was added to the reaction vessel with stirring, and the mixture was reacted for 10 minutes with its temperature maintained at 30° C. On the other hand, a solution of 32.3 kg of sodium hydroxide in 775 liters of deionized water was charged into a separate reaction vessel and maintained at 30° C. A separately formed solution of 120 kg of zinc nitrate (hexahydrate) in 686 liters of deionized water, the solution maintained at 30° C., was added to the separate reaction vessel with stirring, and the mixture was reacted for 10 minutes while holding the mixture at 30° C.

The so prepared slurries containing precipitates of copper and zinc were mixed, and heated to 80° C. with stirring. With its temperature held at 80° C., the mixture was stirred for an additional 30 minutes for aging, and then cooled. The resulting precipitate was filtered by a customary method, and washed. To the filter cake was added 40 kg of alumina sol, and the mixture was kneaded for 40 minutes by a kneader. After the kneading, the resultant mass was dried at 100° C. for 17 hours, then put in a calcination furnace, calcined for 2.5 hours at 370° C., and pulverized and molded in the same manner as in Example 1. The so obtained Cu-Zn-Al three-component catalyst is designated as "catalyst E". A Cu-Zn-Al-B four-component catalyst was prepared in the same manner as described above except that 12.5 kg of boric acid was additionally added to said aqueous solution of zinc nitrate. This four-component catalyst is called "catalyst F".

EXAMPLE 4

A catalyst was prepared in the same way as in Example 3 except that the precipitant for the water-soluble copper salt was changed from ammonium bicarbonate to ammonium carbonate. A Cu-Zn-Al three-component catalyst obtained without the addition of the boron component is designated as "catalyst G," while a Cu-Zn-Al-B four-component catalyst obtained with the addition of the boron component is called "catalyst H".

COMPARATIVE EXAMPLE (Co-precipitation Method)

130 kg of cupric nitrate (trihydrate) and 120 kg of zinc nitrate (hexahydrate) were dissolved in 1670 liters of deionized water, and the solution was maintained at 80° C. To the solution was added a solution (maintained at 80° C.) of 120 kg of soda ash dissolved in 1440 liters of deionized water, thereby to co-precipitate copper and zinc. The precipitate was filtered off, washed, given alumina sol, kneaded, dried and calcined in the same way as in Example 1. The calcination product was pulverized and molded in the same way as in Example 1 to obtain a catalyst, which is called "catalyst I". Also, a catalyst was formed by the same treatments as described above except that the metal components were co-precipitated with sodium carbonate from a mixture of 12.5 kg of boric acid and the aqueous solution of the copper and zinc components mixed. This catalyst is referred to as "catalyst J".

REFERENTIAL EXAMPLE 1

Each of the catalysts A to J prepared in the above-described manner was pulverized to 20 to 40 mesh, maintained at 140° C. in an $N_2$ gas stream, and heated while a synthesis gas was being added slowly so as to avoid violent heat generation, whereafter the catalyst was finally maintained at 240° C. for 3 hours, thereby to reduce the catalyst.

Then, a methanol-synthesizing reaction was performed at a pressure of 70 kg/cm$^2$G, a space velocity of $2\times10^4$ hr$^{-1}$ and a reaction temperature of 260° C. by using the catalyst and a decomposition gas of methanol consisting of 70% $H_2$, 23% CO, 3% $CO_2$, 3.5% $CH_4$ and 0.5% $N_2$. To know the life of the catalyst in short periods, there were measured the catalytic activity exhibited when the synthesis of methanol was performed for 2 hours with the temperature of the catalyst raised to 360° C. and then the temperature was again lowered to 260° C.; the catalytic activity shown when the treatment was further conducted for 4 hours at 360° C. (total time: 6 hours) and then the temperature was lowered again to 260° C.; and the catalytic activity when the treatment was still further conducted for 4 hours (total time: 10 hours) with the temperature raised to 360° C. and then the temperature was lowered again to 260° C. The results measured are shown in Table 1 in terms of the concentration of methanol in the outlet gas.

TABLE 1

| Catalyst | Methanol concentration in outlet gas (mol %) | | | |
|---|---|---|---|---|
| | Initial Period | 360° C., 2 hr | 360° C., 6 hr | 360° C., 10 hr |
| A | 12.0 | 11.3 | 11.0 | 10.7 |
| B | 14.2 | 13.1 | 12.6 | 12.1 |
| C | 12.2 | 11.6 | 11.2 | 11.0 |
| D | 14.0 | 12.9 | 12.5 | 12.1 |
| E | 12.5 | 11.6 | 11.2 | 10.9 |
| F | 15.3 | 13.9 | 13.6 | 13.3 |
| G | 12.3 | 11.3 | 10.9 | 10.7 |
| H | 14.9 | 13.4 | 13.0 | 12.8 |
| I | 10.4 | 9.5 | 8.8 | 8.2 |
| J | 12.6 | 11.8 | 11.4 | 11.2 |

REFERENTIAL EXAMPLE 2

A 100 mm$\phi$ cylindrical drum having a JIS 6-mesh wire gauze applied to the circumferential surface was charged with 10 g of each of the tablet-like catalysts A to J which had been obtained in the Examples and Comparative Example, said catalysts being those before reduction and those after reduction under the conditions described in Referential Example 1. The drum was rolled for 20 minutes at 160 rpm for abrasion of the catalyst. The abrasion rate was calculated from the following equation:

$$\text{Abrasion rate (\%)} = \frac{\text{Amount of sample taken (g)} - \text{Amount of sample remaining in drum (g)}}{\text{Amount of sample taken (g)}} \times 100$$

The results are shown in Table 2.

TABLE 2

| Catalyst | Abrasion rate (%) | |
|---|---|---|
| | Before reduction | After reduction |
| A | 3.6 | 2.0 |
| B | 3.4 | 1.4 |
| C | 4.1 | 2.7 |
| D | 3.8 | 2.5 |
| E | 4.5 | 2.7 |
| F | 4.2 | 2.5 |
| G | 4.8 | 3.5 |
| H | 4.5 | 3.1 |
| I | 7.0 | 81.2 |
| J | 6.1 | 76.8 |

The catalysts I and J can gain the abrasion rate virtually equal to that of the catalysts of A to H only when subjected to the pre-molding twice prior to the compression molding.

REFERENTIAL EXAMPLE 3

Each of the pellet-like catalysts A to J obtained in the Examples and Comparative Example, said catalysts being those before reduction and those after reduction under the conditions described in Referential Example 1, was measured by a small-size material testing machine (a product of Fujii Seiki Co., Ltd.; model PSP-300) for compressive strength in the longitudinal direction (in the direction of central axis) of the catalyst. The results are shown in Table 3.

TABLE 3

| Catalyst | Compressive strength (kg/cm$^2$) | |
|---|---|---|
| | Before reduction | After reduction |
| A | 260 | 215 |
| B | 257 | 220 |
| C | 251 | 212 |
| D | 260 | 221 |
| E | 275 | 280 |
| F | 283 | 312 |
| G | 270 | 277 |
| H | 276 | 295 |
| I | 280 | 210 |
| J | 278 | 235 |

What is claimed is:

1. A process for preparing a catalyst composition comprising a copper oxide, a zinc oxide and an aluminum oxide as essential components, which comprises the following steps:
   (a) a step of precipitating from an aqueous solution of a water-soluble copper salt, a copper component, with the use of ammonium carbonate or ammonium bicarbonate as a precipitant;
   (b) a step of precipitating from an aqueous solution of a water-soluble zinc salt a zinc component, with the use of an alkali hydroxide as a precipitant; and
   (c) a step of calcining a mixture of the precipitates obtained in the steps (a) and (b) in the presence of an alumina precursor compound.

2. The process of claim 1 wherein the steps (a) and (b) are carried out continuously in this sequence or the reverse sequence or the steps (a) and (b) are performed as separate steps.

3. The process of claim 1 wherein the water-soluble copper salt is cupric nitrate.

4. The process of claim 1 wherein the aqueous solution of the water-soluble copper salt contains the copper salt in a concentration of 0.1 to 2.0 mol/l.

5. The process of claim 1 wherein the ammonium carbonate or ammonium bicarbonate is used in a proportion of at least 0.8 equivalent per equivalent of the copper salt to be precipitated.

6. The process of claim 1 wherein the water-soluble zinc salt is zinc nitrate.

7. The process of claim 1 wherein the aqueous solution of the water-soluble zinc salt contains the zinc salt in a concentration of 0.1 to 2.0 mol/l.

8. The process of claim 1 wherein the alkali hydroxide is sodium hydroxide.

9. The process of claim 1 wherein the alkali hydroxide is used in a proportion of at least 0.8 equivalent per equivalent of the zinc salt to be precipitated.

10. The process of claim 1 wherein the steps (a) and (b) are carried out at temperatures of from ambient temperature to about 60° C.

11. The process of claim 1 wherein after the step (a) and/or the step (b), the resulting slurry is aged for at least 5 minutes at a temperature of about 60 to about 100° C.

12. The process of claim 1 wherein the water-soluble boron compound is boric acid or borax.

13. The process of claim 1 wherein the water-soluble boron compound is used at a B/Zn atomic ratio of 0.1–1.5 with respect to the water-soluble zinc salt used in the step (b).

14. The process of claim 1 wherein the alumina precursor compound is alumina sol, or aluminum hydroxide obtained by precipitation from an aqueous solution of a water-soluble aluminum compound.

15. The process of claim 1 wherein the alumina sol has an average particle diameter of at most 1 micron.

16. The process of claim 1 wherein the alumina precursor compound is used at a ratio, calculated as a Cu/Al atomic ratio, in the range of from 3/1 to 70/1 to the copper component in the mixture of the precipitates.

17. The process of claim 1 wherein the calcination is performed at a temperature of at least 300° C.

18. A catalyst composition as prepared by the process of any one of claims 1 to 7 and 17.

19. The catalyst composition of claim 18 which is a Cu-Zn-Al three-component catalyst containing, on a metal atom ratio basis, 30–70% Cu, 15–50% Zn and 1–20% Al.

20. The catalyst composition of claim 18 which is a Cu-Zn-Al-B four-component catalyst containing, on an element atom ratio basis, 30–70% Cu, 15–50% Zn, 1–16% Al and 0.1–5.0% B.

21. The process of claim 1 wherein the aqueous copper salt solution or aqueous zinc salt solution additionally contains a water-soluble boron compound from which a boron component is precipitated.

* * * * *